US006337333B1

(12) United States Patent
Giedlin

(10) Patent No.: US 6,337,333 B1
(45) Date of Patent: *Jan. 8, 2002

(54) METHOD OF TREATING AUTOIMMUNE DISEASE WITH FLUDARABINE-5'-MONOPHOSPHATE

(75) Inventor: Martin A. Giedlin, San Lorenzo, CA (US)

(73) Assignee: Schering Aktiengesellschaft (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 07/965,304

(22) Filed: Oct. 23, 1992

(51) Int. Cl.⁷ .............................................. A61K 31/52
(52) U.S. Cl. ....................................... 514/266
(58) Field of Search ........................................ 514/266

(56) References Cited

FOREIGN PATENT DOCUMENTS

EP          0066918    * 12/1982 .......... A61K/31/62

OTHER PUBLICATIONS

Priebe et al. 114 CA: 748626 1990.*
Lohmeyer et al., Die Medizinische Welt, 44(10):603–606 (1993).
Carrera et al., The Journal of Clinical Investigation, 86(5):1480–1488 (Nov. 1990).
Edwards et al., Journal of Cellular Biochemistry, Suppl., No. 15E p. 155, Abstract No. 103 (1991).
Priebe et al., Cellular Immunology, 129(2):321–328 (Sep. 1990).
Boldt et al., Cancer Research, 44(10):4661–4666 (1984).
Priebe et al., Can. Res. 48:4799–4803 (1988).
Priebe et al., Cell. Immunol. 130:513–519 (1990).
Hirohata et al., Arth. Rheum. 35(2):168–175 (1992).
Vernino et al., Cell Immunol. 139:185–197 (1992).
Granstein et al., Case 19–1992, N. Engl. J. Med. 326(19):1276–1283 (1992).
Carson et al., Blood 62(4):737–743 (1983).
Huang et al., Mol. Pharmacol. 39(4):449–55 (1991).
Schilling, Letters Oncology (Williston Park 5(2):12 (1991).
Communication from European Patent Office re: German Application No. 93 923 964.6–21–12 (corresponding to above–identified U.S. application.
Ruszcak, Der Hautartz, 28:125–131, 1977.
Baker, Barbara S., and Fry, Lionel; "The Immunology of Psoriasis" British Journal of Dermatology (1992), 126, pp. 1–9.
Smith et al., The New England Journal of Medicine, vol. 330, No. 21; "Fludarabine and Psoroasos", May 1994.

* cited by examiner

*Primary Examiner*—Marianne M. Cintins
(74) *Attorney, Agent, or Firm*—Millen, White, Zelano & Branigan, P.C.

(57) ABSTRACT

Fludarabine-5'-monophosphate is useful for the treatment of autoimmune disease, in particular, rheumatoid arthritis.

15 Claims, 12 Drawing Sheets

METHOD OF TREATING AUTOIMMUNE DISEASE WITH FLUDARABINE-5'-MONOPHOSPHATE

BACKGROUND OF THE INVENTION

Autoimmune diseases are characterized by pathogenic immunological responses to autoantibodies. For example, autoimmune mechanisms are recognized as being factors in rheumatoid arthritis, systemic lupus erythematosus, myasthenia gravis, Hashimoto's disease, Addison's disease, psoriasis, pernicious anemia, and multiple sclerosis.

Rheumatoid arthritis (RA) is a chronic systemic autoimmune inflammatory disorder characterized by potentially deforming polyarthritis (1–3). Estimates are that seven million people are afflicted with RA, of whom 1.4 million have definite RA by the American Rheumatology Association (ARA) diagnostic criteria (4). Definite RA is two to three times more frequent in females than in males in the U.S., with the prevalence of the disease increasing with advancing age (5).

The chronic phase of RA is marked by infiltration into the synovium of inflammatory cells and the proliferation of synovial mesenchymal cells (6). The synovium is frequently filled with mononuclear cells, a majority of which are of the helper/inducer T cell subpopulation. Numerous B lymphocytes and plasma cells are also present. The resultant immunoglobulin production from this cell mosaic is predominantly of the IgG isotype (30–60%), as well as IgM (10–30%). The majority of both isotypes is anti-IgG Fc or rheumatoid factor (RF). Immune complexes of the RF type can self-associate and activate or enhance local inflammation, leading to bone erosion and resorption.

Most patients with RA remain on a given therapy for only one to two years (7). The traditional approach to treatment has been to begin patient therapy with aspirin. If this treatment is not effective, patients are then treated with other non-steroidal anti-inflammatory drugs (NSAIDS). If this regimen fails to control the disease's symptoms, then a more aggressive therapy using the "slow-acting" (SAARDS) or "disease-modifying" (DMARDS) drugs, i.e., hydroxychloroquine, intramuscular gold, or D-penicillamine, can be tried. If toxicity or limited effectiveness is seen, the more aggressive and lymphocytotoxic second-line agent azathioprine is administered, followed by methotrexate, and/or cyclophosphamide. Corticosteroids have been used as combination therapy with any of the drugs mentioned above when therapeutic effectiveness is limited.

Recently, many physicians have suggested the use of methotrexate before the use of intramuscular gold or hydroxychloroquine on patients refractory to aspirin but prior to the onset of joint damage. Studies are continuing, however, because the chronic administration of methotrexate results in possible renal toxicity. Furthermore, once the patient begins taking the anti-folate methotrexate, he must continue the drug indefinitely. Those taken off the drug are prone to "flare-up" of the disease. Therefore, an immunosuppressive anti-rheumatic drug with significantly lower toxicity is needed which could be used for longer periods of time.

The potent immunosuppressive drug cyclosporin A (CsA) has recently been used on refractory RA patients, but its usage may be limited due to its nephrotoxicity (8). Other immunotherapies are also being considered, such as monoclonal antibodies, cytokines, and MHC-binding peptides (9). However, at this time, none of the currently available therapies are entirely satisfactory, because of toxicities, opportunistic infections, etc. Drugs with little toxicity at effective doses over long-term use are greatly needed for treatment of autoimmune disease, particularly RA.

SUMMARY OF THE INVENTION

The present invention provides a method of treating autoimmune disease or preventing or ameliorating its symptoms, comprising administering to a patient in need of such treatment an effective amount of fludarabine-5'-monophosphate. In a preferred embodiment, the disease is rheumatoid arthritis.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, wherein:

FIGS. 8a, 8b and 7c show inhibition of cumulative IgM (A), IgG (B), and IgM-RF (C) production in 10 day cultures by FLP or 2-chlorodeoxyadenosine (2CDA)

DETAILED DESCRIPTION OF THE INVENTION

Figure 1A:
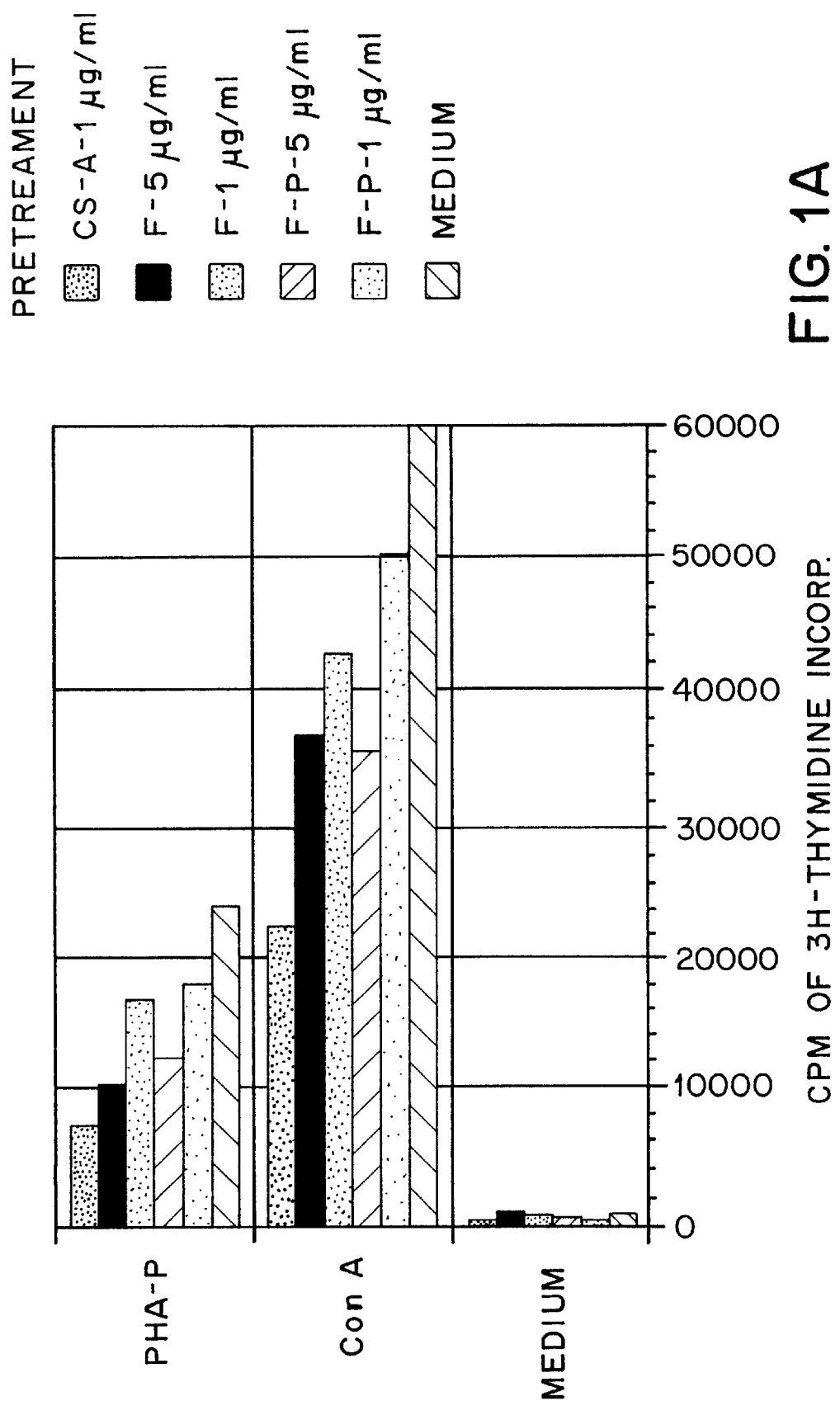
FIG. 1 shows the fludarabine-5'-monophosphate immunosuppressive activity on T and B lymphocyte proliferative response to mitogen following 18 hr drug pretreatment.

Inherited deficiencies of adenosine deaminase (AdA) selectively impair lymphocyte growth and function in humans, resulting in combined immunodeficiency disease (11). There has also been considerable interest in the use of adenosine analogs in the treatment of severe chronic autoimmune disease (10). Furthermore, probably due to the high endogenous kinase levels and low dephosphorylating activity of lymphocytes, inhibitors of AdA or analogs of adenosine have exquisitely specific anti-leukemic or anti-lymphocytic activities (12). Studies with the high affinity AdA inhibitor deoxycorformycin have shown increased plasma deoxyadenosine levels in patients with malignant disease (10). Studies with the adenosine analog 2-chlorodeoxyadenosine (2-CdA) demonstrated growth inhibition of human T-lymphoblastoid cell lines at nanomolar levels (13). Similar effects have been demonstrated with resting and proliferating normal human lymphocytes (14). In addition, published studies have shown that adenosine analogs can affect the expression of HLA-DR antigens on rat macrophages, and various functions of human peripheral blood monocytes (15–16). Indeed, 2-CdA has already been tested, with some success, in patients having autoimmune disease (10).

Purine anti-metabolites have recently shown a great potential as effective chemotherapeutics in lymphoid and other hematopoietic cancers (17–18). The haloadenine nucleotide analog 2-F-ara-AMP or fludarabine-5'-monophosphate (Fludara-I.V.™; hereafter FLP) is the phosphate derivative of 9-B-D-arabinofuranosyl adenine (ara-A) (19–20). It has effected dramatic improvement in both complete and partial response rates in patients with B lymphoblastoid chronic lymphocytic leukemia (B-CLL) (48). The typical B-CLL is characterized by the monoclonal expansion (κ or λ light chain) of cells with surface membrane IgM and IgD, CD19, CD20, and CD24, and the pan-T cell surface marker CD5 (Leu 1). These B-lymphoblastoid cells are CD2, CD3, CD4, and CD8 negative (21–23).

Analogous to B-CLL, a significant number of the B lymphocytes in the RA lesion are also CD20/CD5 positive. This phenotype is reflected in increased numbers of the CD20/CD5 B lymphocyte subpopulation in the peripheral blood of patients with RA, SLE, and other autoimmune diseases (24–29) over that seen with normal controls. In phase I/phase II clinical trials of refractory RA using monoclonal antibodies directed against lymphocytes expressing CD5 (e.g., anti-CD5-ricin A chain) monitored for clinical efficacy by measuring the frequency of CD3/CD5 positive cells in peripheral blood lymphocytes, transient decreases in those subpopulations expressing CD5 correlate with significantly improved clinical parameters (30–32). In addition, recent publications have identified the ligand for CD5, called CD72. CD72 is expressed on all B lymphocytes and the data suggest a role for CD5-CD72 interactions in the activation and regulation of CD5-B lymphocytes (33). Thirdly, the novel disease-modifying drug lobenzarit (disodium 4-chloro-2,2'-iminodibenzoate or CCA) has been shown to have clinical efficacy in treatment of RA (55, 56). Recent studies have demonstrated that this drug suppressed the production of IgM-RF as well as IgM at therapeutic concentrations of drug (57).

Preliminary studies were performed in vitro. Peripheral blood mononuclear cells obtained from packed leukocyte preparations were enriched for T and B lymphocytes using neuraminidase-treated sRBC rosetting (49). Eighteen-hour pretreatment of both T and B lymphocytes with fludarabine suppressed their ability to respond to mitogens. Dose response studies with cultures continuously exposed to either FLP or 2-chloro-deoxyadenosine (2CDA) demonstrated that both drugs have the ability to suppress the mitogen response at levels of 0.5 µg/ml. Flowcytometric studies of CD20, CD20/CD5, and CD3/CD5 lymphocyte subpopulations at the end of either a 48 hr or 5 day mitogen stimulation culture period suggested that FLP had similar suppressive effects on CD5 expression to those seen with 2CDA. Culture supernatants examined by enzymatic immunoassay (EIA) for cumulative IgM, IgG, and IgM-RF production demonstrated a dose-related decrease by both agents in the accumulation of all three species in both 5 and 10 day Staphylococcus aureus Cowan I (SAC) rIL-2 (recombinant human IL-2) cultures. Viable cultured cells examined by flowcytometry at the end of the above 5 and 10 day culture periods suggested that the CD20/CD5 subpopulations were decreased by both agents in a drug dose dependent manner, and that the CD20/CD5/sIgM and CD20/CD5/sIgG subsets were similarly affected. (Data not shown.)

These data suggest that FLP has properties which are useful for the treatment of autoimmune disease. The drug demonstrates both a cytotoxic and immunosuppressive effect on both T and B lymphocytes, and therefore can be used as a first or second line agent in those autoimmune diseases, e.g., particularly where slow acting anti-rheumatic disease (SAARD) therapy has reduced disease-associated symptoms.

Current SAARD therapies include disodium gold thiomalate ($Na_2AuTM$), the antifolate methotrexate, L-penicillamine, sulfasalazine, cyclophosphamide, and Cyclosporin A (50).

By "autoimmune disease" as used herein is meant any one of a variety of disease states or conditions involving the inappropriate and/or detrimental induction of autoantibodies or activated T-lymphocytes against constituents of the patient's own body.

By "rheumatoid arthritis" as used herein is meant the variety of symptoms classically understood by physicians to indicate the disease. For example, according to the American Rheumatism Association, there are generally 11 symptoms of RA, 7 of which indicate a diagnosis of classic RA. Symptoms 1–5 are fulfilled by observation of the continuous presence of these signs or symptoms for at least 6 weeks:

1. Morning stiffness
2. Pain with motion or tenderness in at least one joint
3. Swelling of at least one joint
4. Swelling of at least one other joint
5. Symmetric joint swelling
6. Subcutaneous nodules on any bony prominences, extensor surfaces, or justa-articular regions
7. Roentgenographic changes typical for RA
8. Positive agglutination test for RF
9. Poor mucin precipitation test from synovial fluid
10. Histological changes in synovium
11. Histological changes in nodules However, other criteria may also be applied to arrive at a conventional diagnosis of RA.

In the prophylactic aspect of this invention, hosts will include patients conventionally considered to be at risk for autoimmune disorders, e.g., those with a family history of such disorders, HLA-DR (Class II) or HLA-B (Class I) MHC antigen associations (53), sex, age, and previous exposure to either particular viral or bacterial pathogen (54).

Fludarabine-5'-monophosphate is commercially available as Fludara® (Berlex Laboratories, NJ). It can be prepared, e.g., according to the process disclosed in U.S. Pat. Nos. 4,210,745 and 4,357,324. It is known for use as an anti-leukemic and antiviral agent (see, e.g., U.S. Pat. No. 4,188,378).

The administration of fludarabine-5'-phosphate for treatment of autoimmune disease, e.g., rheumatoid arthritis, is analogous to administration of methotrexate. In the treatment of RA, methotrexate is given in the dose range of 5–15 mg/week. This is in contrast to the oncology dose of 3 five-day doses of 15–30 mg/day with one week between doses (PDR 92).

In general, fludarabine-5'-phosphate is administered for the treatment of or prophylactic administration for autoimmune diseases in amounts which are generally lower than are typically administered for treatment of leukemia. The current dose for the treatment of B cell CLL is 25 mg/kg/day for 5 days followed by a month of rest before the beginning of the next course. The mean number of courses is 3–5 per treatment. Therefore, suitable dosages for treatment of RA are 1 to 10 mg/kg/day, preferably 1 to 7.5 mg/kg/day, most preferably 1 to 5 mg/kg/day. One course of treatment for RA would be one dose per week for four consecutive weeks, with a rest of one month before the next course. In support of using lower doses of Fludarabine in the treatment of RA, studies of B-CLL patients treated with Fludarabine showed the peak concentration of F-ara-ATP in the lymphocytes was 10-fold higher than the serum peak (55).

Equivalents of Fludarabine-5'-monophosphate include the non-phosphorylated compound as well as the multiply phosphorylated compound.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, are hereby incorporated by reference.

EXAMPLES

Materials and methods

1. Reagents

Recombinant human IL-2 (*E. coli*) was obtained from Boehringer Mannheim (#799-068, L#606448, 100 U/mg). The *Staphylococcus aureus* Cowan I strain was obtained from Calbiochem (Pansorbin, #507858, La Jolla, Calif.). The fludarabine-5'-phosphate was a generous gift from Berlex Laboratories (fludarabine-5'-phosphate, L#156-07-0005, Alameda, Calif.).

2. Cell Separation

Packed leukocyte preparations (Stanford Blood Bank, Palo Alto, Calif.) containing approximately $5\times10^8$–$10^9$ leukocytes were obtained by leukophoresis from normal volunteers. Approximately 20–35 ml of packed leukocytes were diluted with 100 ml of serum-free RPMI-1640 (Whittaker, Walkersville, Md.) supplemented with 2 mM L-glutamine, 0.1 mM non-essential amino acids (NEAA), 1.0 mM sodium pyruvate, Pen G (100 U/ml), Strep (100 µg/ml), and 50 mM 2-mercaptoethanol. Twenty ml of the diluted leukocytes were layered over 15 ml of lymphocyte separation medium (LSM, Organnon Teknika, Durham, N.C.) and centrifuged for 20 min at 2000 rpm (850× g, Sorval RT6000B, DuPont, Newtown, Conn.).

The interface layer containing the lymphocytes, monocytes and some contaminating granulocytes, and now referred to as PBMC, were removed, pooled, and washed three times with serum-free medium to remove contaminating platelets. The washed PBMC's were counted and viability determined by trypan blue exclusion. An aliquot of cells were removed for phenotypic analysis by flow cytometry using the Becton Dickinson FACScan flowcytometer, Simulset software, and CD-specific antibody reagents (see Table I).

TABLE I

Monoclonal Antibody Reagents

| MoAb | Isotype | Specificity |
| --- | --- | --- |
| anti-CD5 | IgG2a | T,B lymphocytes |
| anti-CD20 | IgG1 | B lymphocytes |
| anti-huIgG | IgG2b | Hu IgG (H & L) |
| anti-huIgM | IgG1 | Hu IgM (µ chain) |
| anti-CD14 | IgG2b | Monocytes, macrophages |
| anti-CD45 | IgG1 | Leukocytes |
| anti-CD3 | IgG1 | T lymphocytes |

The contaminating monocytes and granulocytes were removed from the PBMC by incubation with 0.9085 mg/ml leucine-methyl ester (LME, Sigma, St. Louis, Mo.) at RT for 35 minutes. The PBMC were then washed three times with serum-free medium and the clumps removed by a 70 µm nylon screen (Falcon #2350). The cells were counted and adjusted to less than $1\times10^7$ cells/ml in medium containing 10% FBS. The removal of T cells was accomplished by dispensing approximately 5–8 ml of LME-treated PBMC to a 50 ml centrifuge tube along with 2.5–4 ml of fresh neuraminidase (GIBCO #840-7050AA, Grand Island, N.Y.) treated sRBC (Cedarlane #CL2581, Hornby, Ontario, Canada) and 2.5–4 ml of heat in-activated FBS. This mixture was incubated at 37° C. for 10 min and then CFG for 10 min at 1000 rpm (200× g). The pellets were then incubated on ice for 2–18 hr. The pellets were gently resuspended with a 10 ml pipette and under-layed with 10 ml of LSM and centrifuged for 25 min at 1500 rpm (470× g). The B cells at the medium-LSM interface were extracted, washed once in medium with 10% FBS (S-10), and then either immediately put into culture or re-rosetted. The resulting T cell (resetting cells) were approximately 90–98% CD3 positive, with <5% CD19 and <1% CD14 positive cells. The resulting B lymphocyte (non-resetting) fractions were 60–80% CD19, 50–75% CD20, and 20–30% CD20/CD5 positive, with <20% CD3 and <1% CD14 positive cells.

A second method of B lymphocyte enrichment utilized the ability of nylon wool to retard the elution of the B cells through a column. Briefly, $5\times10^8$ LME-treated PBMC's in 3 ml pre-warmed S-10 medium were loaded onto a 20 ml syringe containing 1 g of washed, pre-warmed Nylon Wool (Robbins Scientific Corp., Sunnyvale, Calif.). The syringe column was then incubated for 1 hr at 37° C. and the T cell fraction eluted with 100 ml of pre-warmed S-10. The B cell fraction was then recovered with three 50 ml washes of ice-cold S-10, followed by vigorous agitation of the nylon wool and elution with the syringe plunger. Both fractions were then washed once in S-10 and counted.

3. Culture Conditions

Approximately $5\times10^5$–$1\times10^6$ PBMC, enriched T, or B lymphocytes were cultured in 1 ml of S-10 in Falcon 10×75 mm capped polypropylene tissue culture tubes (Falcon #2063) for the appropriate times at 37° C. in a humidified 5% $CO_2$/air atmosphere. Recombinant IL-2 (rIL-2) was used at 50 U/ml and SAC was at a final concentration of 1/60,000. The mitogens phytohemagglutinin (PHA-P) (Pharmacia, #27-3707-01, Uppsala, Sweden) and pokeweed mitogen (PWM, Pharmacia, #27-3702-01) were used at 5 µg/ml and 10 µg/ml, respectively.

In FIG. 1, freshly isolated PBMC were enriched for T and B lymphocytes using Nylon Wool (see Materials and Methods, Example A). The enriched lymphocyte subpopulations were then incubated for 18 hrs at 37° C. with various concentrations of drug. At the end of the pretreatment period, the cell samples were washed, adjusted to $2\times10^5$ viable cells/ml, and cultured at $1\times10^4$/well in flat (B cells) or round (T cells) bottomed 96 well microtiter plates in 200 µl/ml. The T cells were incubated for 3 days with PHA-P (5 pg/ml) or Con A (5 µg/ml) and the B cells were cultured for 6 days with either PWM (2 µg/ml) or SAC (1/60,000). 1 µCi of $^3$H-thymidine was added per well during the last 18 hr of culture. The wells were then harvested onto glass fiber filters, and counted in 7 ml of Cytoscint (ICN) on the LKB 1219 Rackbeta scintillation counter. The results are expressed as the mean cpm of triplicate wells. The standard deviation of the mean was less than 0.05%.

In FIG. 2, peripheral blood mononuclear cells enriched for either T (top) or B (bottom) lymphocytes were continuously cultured with the appropriate concentrations of drug for 3 or 6 days, respectively. The mitogen PHA-P was used at 5 µg/ml and the mitogen PWM was used at 1 µg/ml. The wells were pulsed and harvested as described above.

4. Lymphocyte Phenotypic Staining

Cells were washed once in citrate buffered saline (C-BSS) and $10^5$–$10^6$ cells per sample were aliquoted for staining. For direct immunofluorescence, 10 ml of either FITC- or PC-conjugated CD-specific mouse monoclonal antibody (Becton Dickinson, San Jose, Calif.) were added to cells in 50–100 ml of C-BSS and incubated at RT for 30 min. The samples were then washed once in 2 ml C-BSS, resuspended in 0.5 ml C-BSS and acquired on a B/D FACScan Flowcytometer using either Simulset or Lysis II software. During analysis of data files, lymphocytes were discriminated from monocytes and dead cells on the basis of their forward light scatter (FCS) properties and high positivity with anti-CD45 and anti-CD14 (leucogate).

Figure 3:
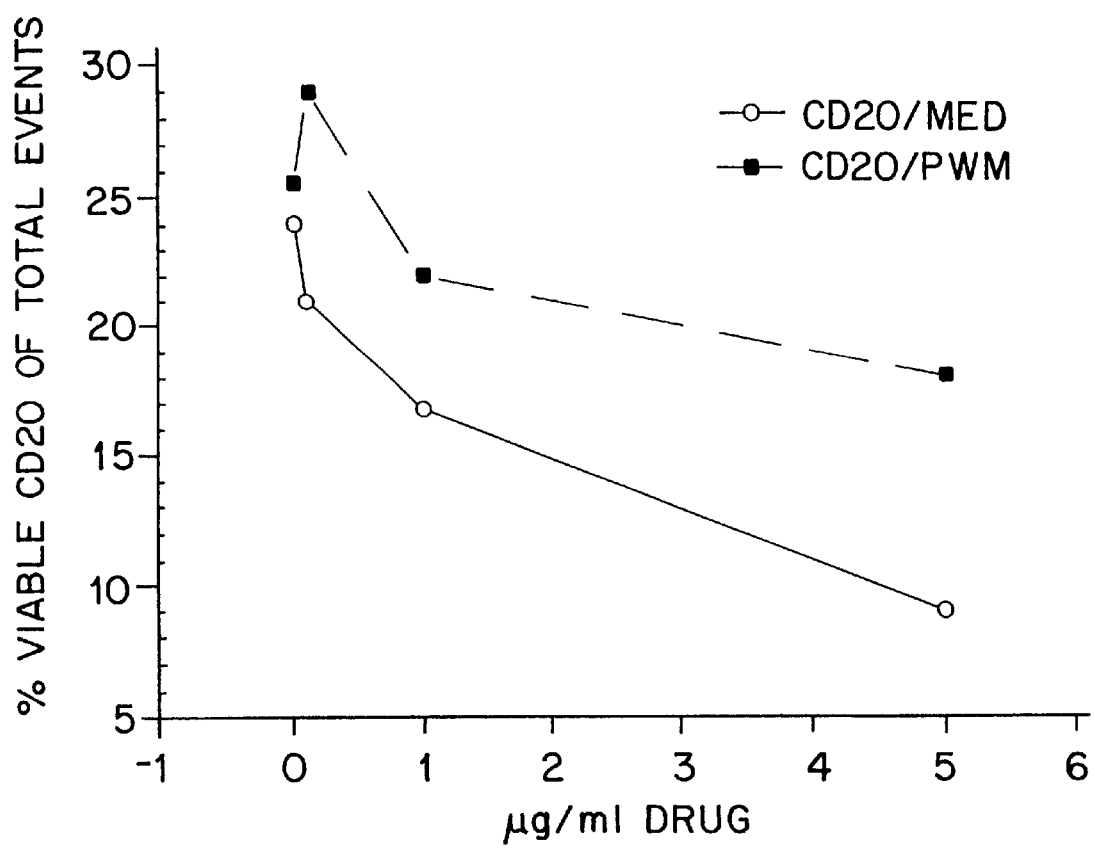
FIG. 3 shows fludarabine-5'-phosphate (FLP) toxicity toward stimulated and nonstimulated PBMC enriched for B lymphocytes.

In FIG. 3, freshly isolated PBMC enriched for CD20 positive B lymphocytes (50% CD19, 45% CD20, 10% CD20/CD5 and 30% CD3/CD5) were cultured over 48 hr with various concentrations of FLP with and without PWM (5 µg/ml). The cells were washed once in C-BSS, and resuspended in 0.5 ml C-BCC with 5 µl of PI. Percent viable CD20 positive cells were determined by analysis on a FACScan using the LYSIS II software. Results are expressed as percent of total gated viable cells.

Figure 4:
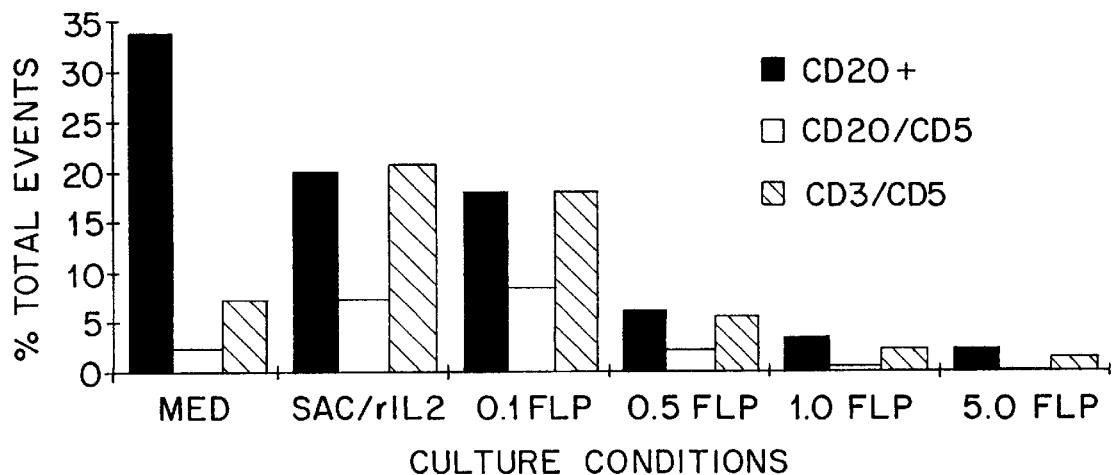
FIG. 4 shows Fludarabine (FLP) toxicity towards CD5 positive CD20 and CD3 lymphocyte subsets during SAC (1/60,000)+rIL-2 (50 U/ml) culture at various concentrations of FLP.

In FIG. 4, at the end of the culture period, the cells were washed, fixed with 1% formalin/PBS, and stained with mouse monoclonals anti-CD20 (PE), anti-CD3 (PE), and anti-CD5 (FITC). The stained samples were analyzed on a FACScan flowcytometer using LYSYS II software. Viable cells were gated and results are expressed as percent of total viable events acquired.

For viability determination of unfixed samples, 5 µl of a 500 mg/ml stock—solution of propidium iodide (PI) was added to the samples (0.5 ml)—immediately before acquisition.

5. Three color indirect immunofluorescence staining of human B lymphocyte subsets The specificities of the monoclonal antibodies used in this technique are presented in Table I. All reagents were prepared at Becton Dickinson Immunocytometry Systems (San Jose, Calif.). The Texas Red dye, RED 613 (TR613), covalently conjugated to R. phycoerythrin (R.PE), was conjugated to Streptavidin. The conjugate used in these experiments had a fluorochrome/protein ratio of 1.04.

i. Three color staining procedure.

One million mononuclear cells in a total of 100 µl of diluent were placed into a 12×75 mm polystyrene culture tube. Ten micrograms of FITC-conjugated antibody and/or 10 µg of PE-conjugated antibody, and/or 10 µg of biotinylated antibody in a total volume of 100 µl were added to the appropriate tube. The tubes were then vortexed and incubated for 30 min at RT. The samples were then washed in 2 ml of diluent, the supernatant removed, and 1 µg of the Streptavidin-TR613 added in a total volume of 100 µl of diluent. After 30 min incubation at RT, the cells were washed in 2 ml of diluent and the cell pellet resuspended in 1 ml of 1% formalin/PBS. The fixed cells were stored in the dark at 4° C. until acquisition and analysis. Phosphate buffered saline (9.5 mM phosphate, $Mg^{++}/Ca^{++}$ free, pH 7.2) was used as diluent. Controls consisted of cells stained only with TR613 Streptavidin or cells stained with a FITC- or PE-conjugated isotype matched IgG anti-KLH monoclonal antibody.

ii. Three color flowcytometric analysis

Three color flowcytometric analysis was performed using the FACScan (Becton Dickinson, San Jose, Calif.). Briefly, an argon-laser (15 mW, 488 nm) was used for excitation of FITC, PE, and TR613. Fluorescence emission for FITC, PE, and TR613 were detected by selectively collecting 530+15 nm (FITC), 575+12 nm (PE), and 630+13 nm (TR 613). Forward scatter (FCS), side scatter (SSC), green fluorescence (FITC), orange fluorescence (PE), and red fluorescence (TR 613) were measured by LYSYS II and stored in the acquisition mode for re-analysis by LYSYS II and the CONSORT 32 computer system (Becton Dickinson Immunocytometry Systems, San Jose, Calif.). In determining the percent of positive staining cells, a marker was set on the appropriate control dot plot such that 1% or less of the cells were in the quadrant(s) above the x,y markers. By using this as a reference point, the percent of cells in the specific antibody-staining sample dot-plot was calculated. Twenty thousand (20,000) events were acquired for each sample. Populations of cell subsets were reported as percentage of total lymphocytes. Data for normal ranges are reported in Table III.

6. Gating Techniques and Relationships of CD5, CD20, sIgM and sIgG

During analysis of the data files, lymphocytes were discriminated from monocytes and dead cells on the basis of their characteristic forward light scatter properties.

Lymphocytes were also discriminated from monocytes on the basis of monocytes' high positivity on immunofluorescence histogram (e.g., anti-CD45 FITC on the x-axis and anti-CD14 PE on the y-axis). The lymphocytes were selected out by setting a gate on forward light scatter and side scatter dot plot. To quantify the CD20 and CD5 lymphocyte subsets identified by the specific fluorochrome-conjugated antibodies, data were re-analyzed with the lymphocyte gate set on the immunofluorescence dot plot of CD5 FITC and CD20 PE which displayed CD5 FITC+/CD20 PE– population (LR quadrant), CD20 PE+/CD5 FITC– population (UL quadrant) based on the FITC/PE control sample. The second gate was set on the CD5 FITC+/CD20 PE+ population (UR quadrant). By applying both lymphocyte and CD5 FITC+/CD20 PE+ population gates on the immunofluorescence dot plot of CD20 PE and Hu IgG TR613, it was possible to determine the expression of sIgG on the CD5/CD20 lymphocyte subsets based on the TR613 control. In a similar manner, gates were set on the immunofluorescence histogram of CD20 PE and Hu IgM TR613 to examine the expression level of sIgM on the CD5/CDC20 lymphocyte subsets. Subsequently, it was possible to calculate the percentage of cells constituting these subsets of the total number lymphocytes acquired.

This analysis shows a decrease in the CD5/CD20 lymphocyte subsets that express both surface IgM and surface IgG. These results parallel those seen in secreted IgM-RF and IgG in patients in remission. (Data not shown.)

7. Enzyme-linked immunosorbant assay (EIA)

Figure 5:
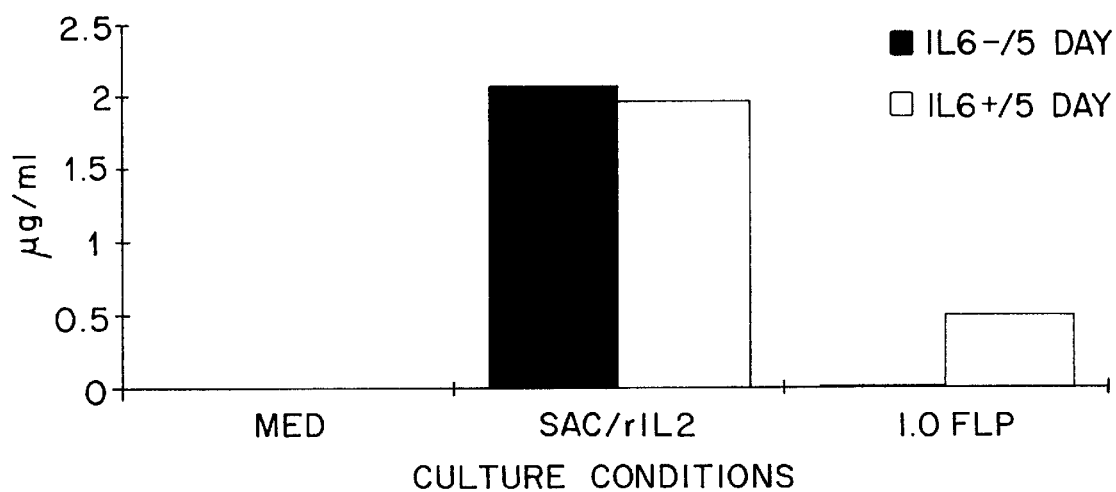
FIG. 5 shows inhibition of cumulative IgM production in 5 day in vitro cultures by FLP.

In FIG. 5, peripheral blood mononuclear cells (PBMC) enriched for B lymphocytes (BC89; 60% CD19, 59% CD20, 8% CD3) were continuously cultured at $5 \times 10^5$/ml and stimulated with *Staphylococcus aureus* Cowan I (SAC) plus interleukin 2 (IL-2) (50 U/ml) in the presence of 1.0 μg/ml of FLP. Recombinant IL-6 was added to 50 U/ml. After the culture period, the supernatants were harvested and assayed for huIgM by EIA. Results shown are from 1 representative experiment of 5 different experiments conducted with 5 different sources of leukocyte preparations.

Figure 6:
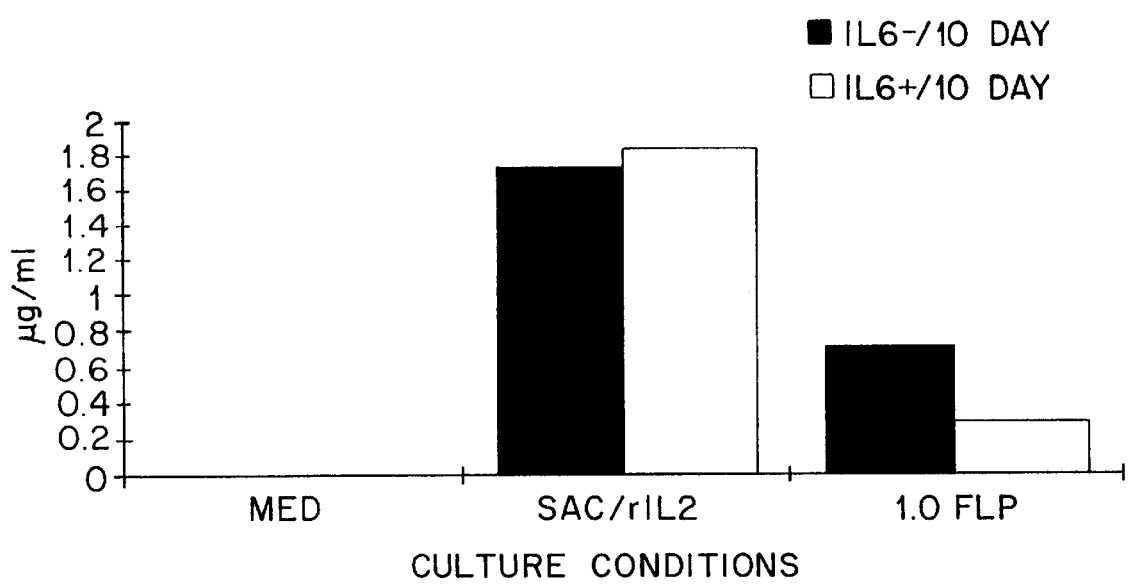
FIG. 6 shows inhibition of cumulative IgM production in 10 day in vitro cultures by FLP.

In FIG. 6, peripheral blood mononuclear cells (PBMC) enriched for B lymphocytes (BC88; 46% CD19, 41% CD20, 35% CD3) were continuously cultured at $5 \times 10^5$/ml and stimulated with *Staphylococcus aureus* Cowan I (SAC) plus interleukin 2 (IL-2) (50 U/ml) in the presence of 1.0 μg/ml of FLP. Recombinant IL-6 was added to 50 U/ml. After the culture period, the supernatants were harvested and assayed for huIgM by EIA. Results shown are from 1 representative experiment of 5 different experiments conducted with 5 different sources of packed leukocyte preparations.

Figure 7A:
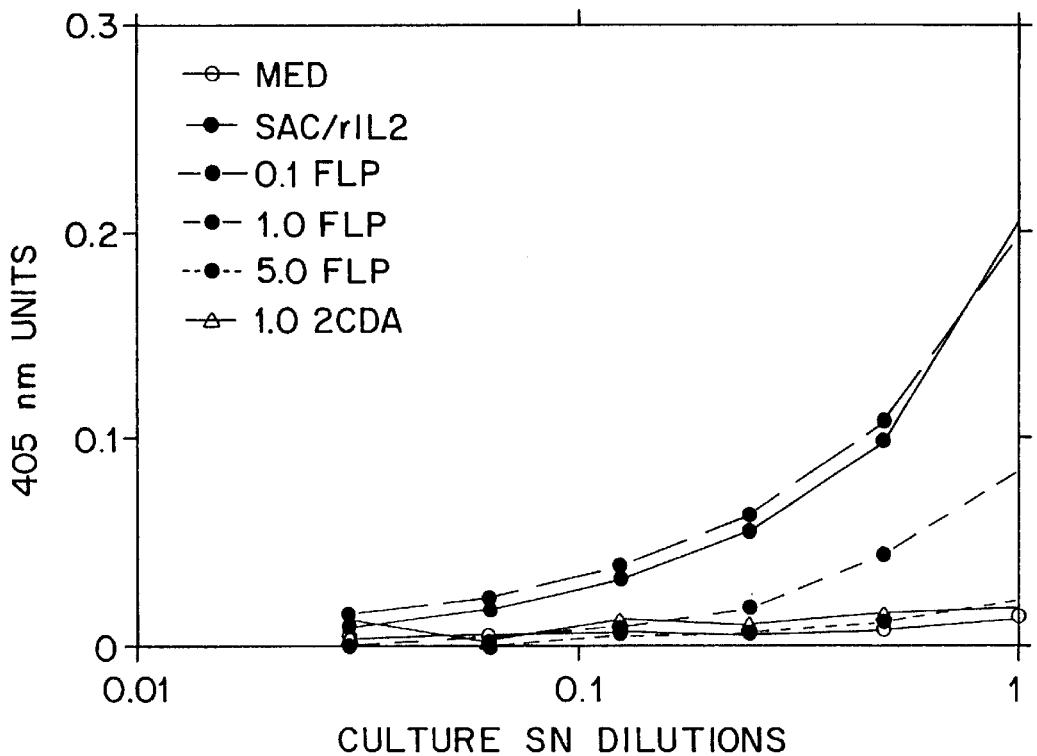
FIGS. 7a, 7b and 7c show inhibition of cumulative IgM (A), IgG (B), and IgM-RF (C) production in 5 day cultures by FLP or 2-chlorodeoxyadenosine (2CDA)

In FIG. 7, peripheral blood mononuclear cells (PBMC) enriched for B lymphocytes (BC92; 35% CD19, 33% CD20, 35% CD3) were continuously cultured for 5 days in either medium alone, *Staphylococcus aureus* Cowan I (SAC) plus interleukin 2 (IL-2) (50 U/ml), or SAC plus IL-2 in the presence of various concentrations of FLP or 2-chlorodeoxyadenosine (2CDA). After 5 days of culture, the supernatants were harvested and serial dilutions of supernatant assayed for huIgM and huIgG by EIA. The presence of IgM rheumatoid factor (IgM-RF) was determined by EIA using the Vectastain Biotin-Streptavidin amplification system. Results are reported as O.D. 405 nm units. Nonspecific binding of neat supernatant to uncoated wells was <0.05% of that seen with the respective coated wells. The results shown are from 1 representative experiment of 4 separate experiments conducted with 4 different sources of packed leukocytes.

Figure 8A:
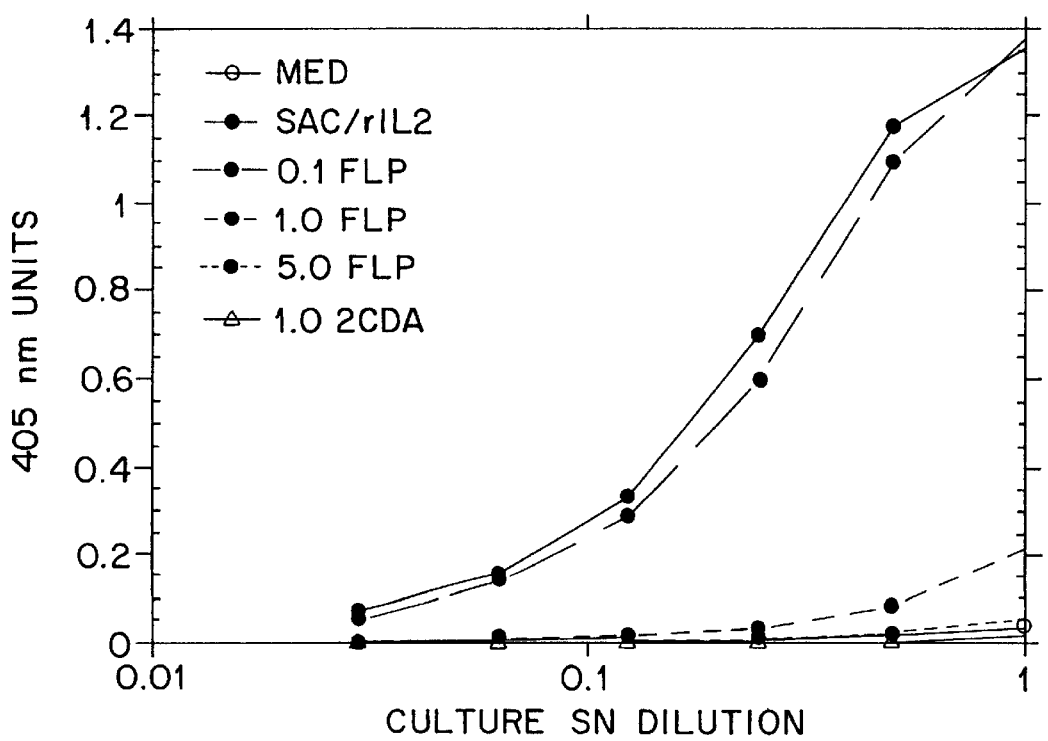
Figure 8B:
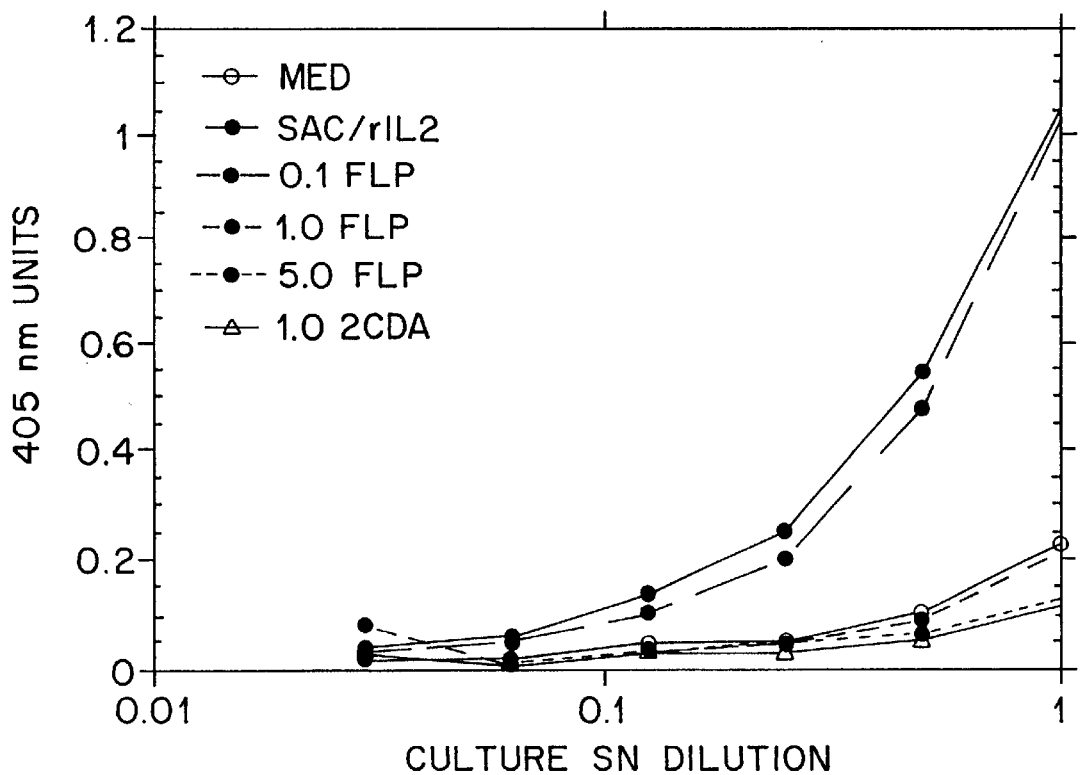

In FIG. 8, peripheral blood mononuclear cells (PBMC) enriched for B lymphocytes (BC92, 35% CD19, 33% CD20, 35% CD3) were continuously cultured for 10 days in either medium alone, *Staphylococcus aureus* Cowan I (SAC) plus interleukin 2 (IL-2) (50 U/ml), or SAC plus IL-2 in the presence of various concentrations of FLP or 2CDA. At the end of the culture period, the supernatants were harvested and serial dilutions assayed for huIgM, huIgG, and IgM-RF by EIA. The cells were phenotyped by flowcytometry. Results are reported as O.D. 405 nm units. Nonspecific binding of neat supernatants to uncoated wells was <0.5% of that seen with parallel coated wells. The results shown are from 1 experiment representative of 3 separate experiments conducted with 3 different sources of packed leukocytes.

Figure 9A:
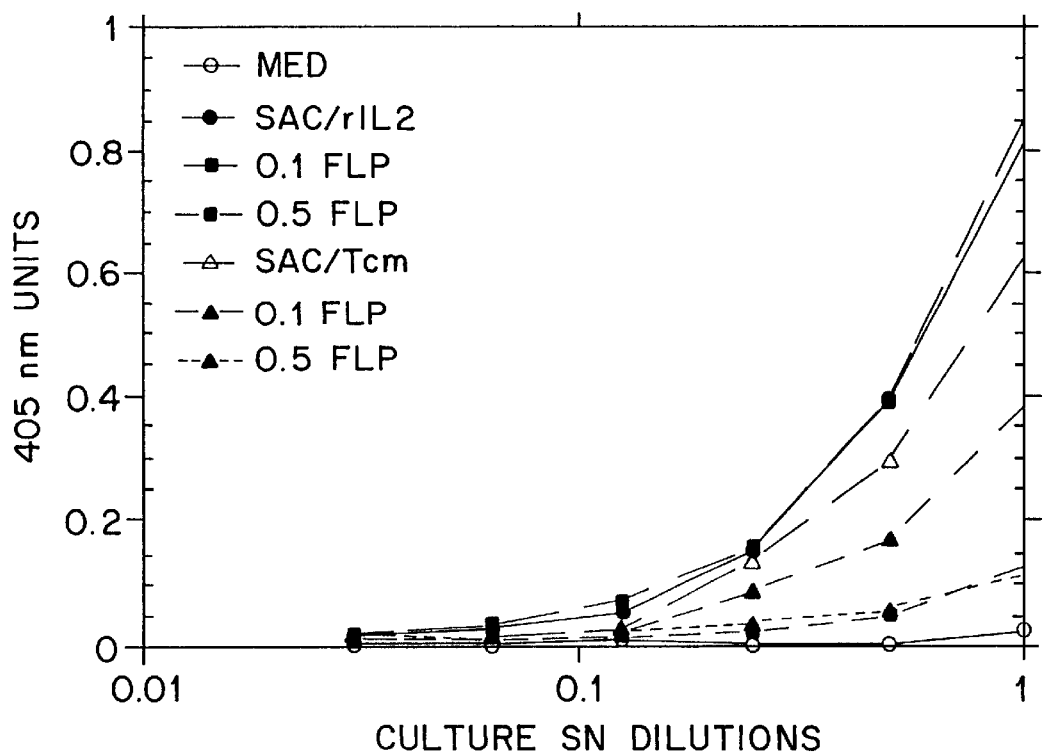
FIGS. 9a, 9b and 9c show inhibition of cumulative IgM (A), IgG (B), and IgM-RF (C) production in 5 day cultures of PBMC stimulated with *Staphylococcus aureus* Cowan I plus interleukin 2 or T lymphocyte conditioned medium.
Figure 9B:
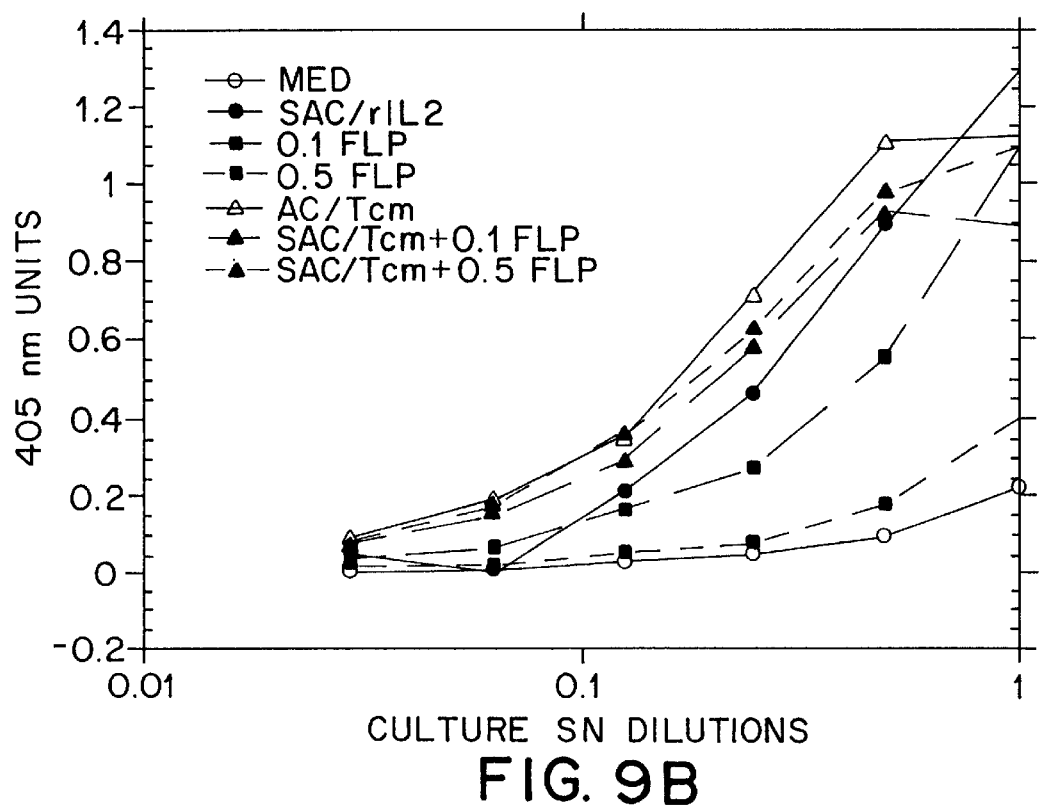
Figure 9C:
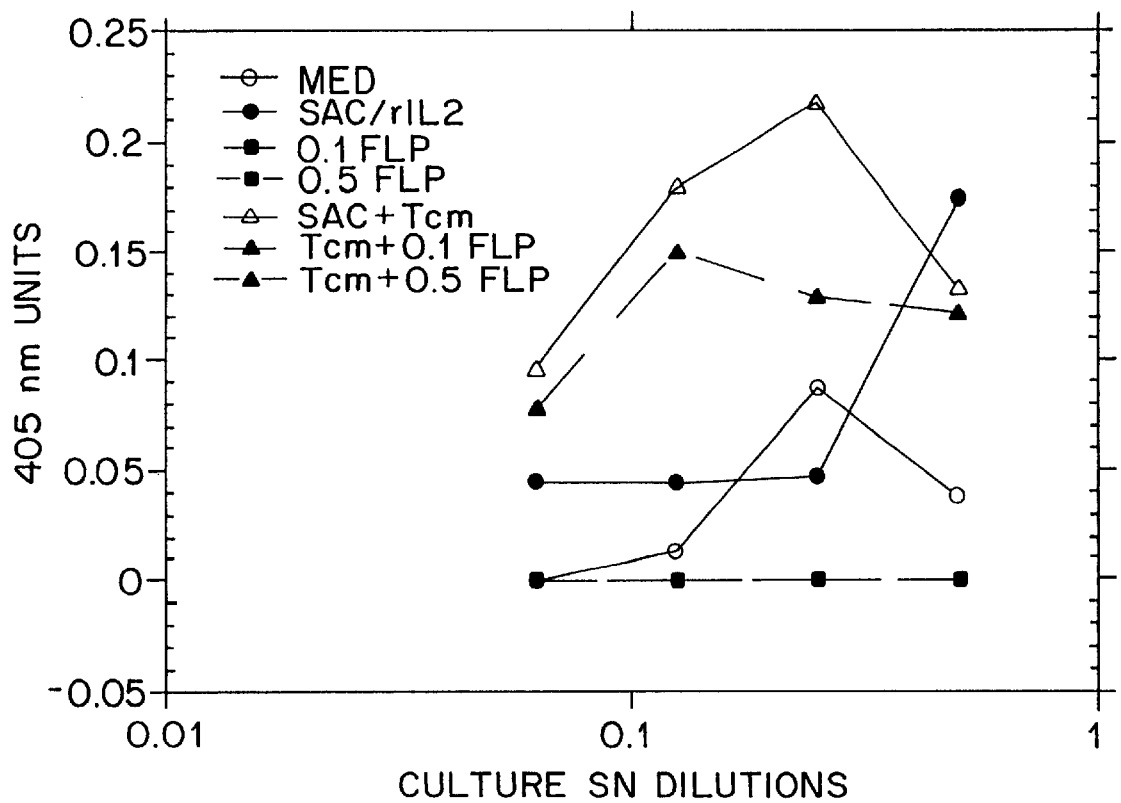

In FIG. 9, peripheral blood mononuclear cells (PBMC) (BC93; 22% CD19, 20% CD20, 78% CD3) were continuously cultured for 5 days in either medium alone, *Staphylococcus aureus* Cowan I (SAC) plus interleukin 2 (IL-2) (50 U/ml) or 20% T cell conditioned medium (Tcm) in the presence of various concentrations of FLP. At the end of the 5 day culture period, the supernatants were harvested and serial dilutions assayed for huIgM, huIgG, and IgM-RF by EIA. The results are reported as O.D. 405 nm units. Nonspecific binding of neat supernatants to uncoated wells was <0.05% of parallel coated wells. The results shown are from one representative experiment.

i. Total IgM and IgG determination

Immulon-2 (Dynatek Laboratories, #011-010-3450, Chantilly, Va.) flat-bottom 96 well microtiter plates were coated with 100 μl/well of a 2 μg/ml solution of goat F(ab')$_2$ anti-HuIgM (μ chain, CALTAG #H15100, So. San Francisco, Calif.) or goat F(ab')$_2$ anti-HuIgG (Fc sp., CALTAG #H10100) in 0.1 M sodium carbonate buffer, pH 9.6 overnight at 4° C. Uncoated wells were incubated with the carbonate buffer alone. The plates were rinsed and then incubated with 100 μl/well of 0.1% BSA/PBS for 1 hr at RT. The plates were rinsed twice with PBS and then incubated for 2 hrs at RT with the respective serial dilutions of culture supernatant and human IgM or IgG standards (Sigma, St. Louis, Mo.). All dilutions were made in complete S-10 medium (see above). At the end of the incubation period, the plates were rinsed 3 times with PBS/0.05% Tween-20. 100 μl of a 1/500 dilution of goat F(ab')$_2$ anti-IgM (m) or anti-IgG (H+L) conjugated with alkaline phosphatase (Fisher Biotech, #OB1210-ALPH and #OB1220-ALPH, Pittsburg, Pa.) was added to each well and incubated for 1 hr at RT. The plates were rinsed 3–5 times with PBS/0.05% Tween-20 and 100 μl/well of p-nitrophenyl phosphate substrate (Bio-Rad, Richmond, Calif.) was added and incubated for 30 min. The wells were read at 405 nm with an InterMed NJ-2000 immunoreader. The concentration of sample IgM or IgG was calculated off of a standard curve using the XFROMY linear regression analysis on RS-1 (VAX-VMS). Nonspecific binding was determined from low-dilution samples incubated in parallel in uncoated wells (<0.005% O.D. 405 nm of coated wells). Results are reported as either μg/ml antibody or O.D. 405 nm units.

ii. IgM-RF determination

The procedure to determine amounts of IgM-RF in culture supernatants was a modification of the methodology described above. Briefly, plates were coated with 100 μl/well of a 2.4 μg/ml solution of human IgG Fc fragments (Jackson ImmunoResearch, Chrompure #009-000-008) in 0.1 M sodium carbonate, pH 9.6 overnight at 4° C. The wells were blocked with 0.1% BSA/PBS for 1 hr at RT, and then serial dilutions of culture supernatant were cultured at 100 μl/well for 18–48 hrs at RT. A Vectastain Human IgM ABC-AP kit (Vector Laboratories, #AK-5009, Burlingame, Calif.) was used to develop the plates. Sera from patients with RA (IgM-RF titer greater than 750) were used as dilution standards. Results are reported as O.D. units at 405 nm.

Example 1

Effect of FLP Treatment on T and B Cells in Discussion Culture

Previous in vivo studies have demonstrated that FLP can decrease both the normal T and B cell compartments in patients treated for B-CLL (17). It was therefore of interest to further investigate the effect of FLP on normal T and B lymphocyte populations enriched from peripheral blood. Particularly of interest was the ability of the drug to suppress immune function in addition to its cytotoxic properties.

Peripheral blood mononuclear cells obtained from normal donors as packed leukocyte preparations were enriched for T and B lymphocytes and pretreated with drug for 18 hrs prior to mitogen stimulation.

Figure 1B:
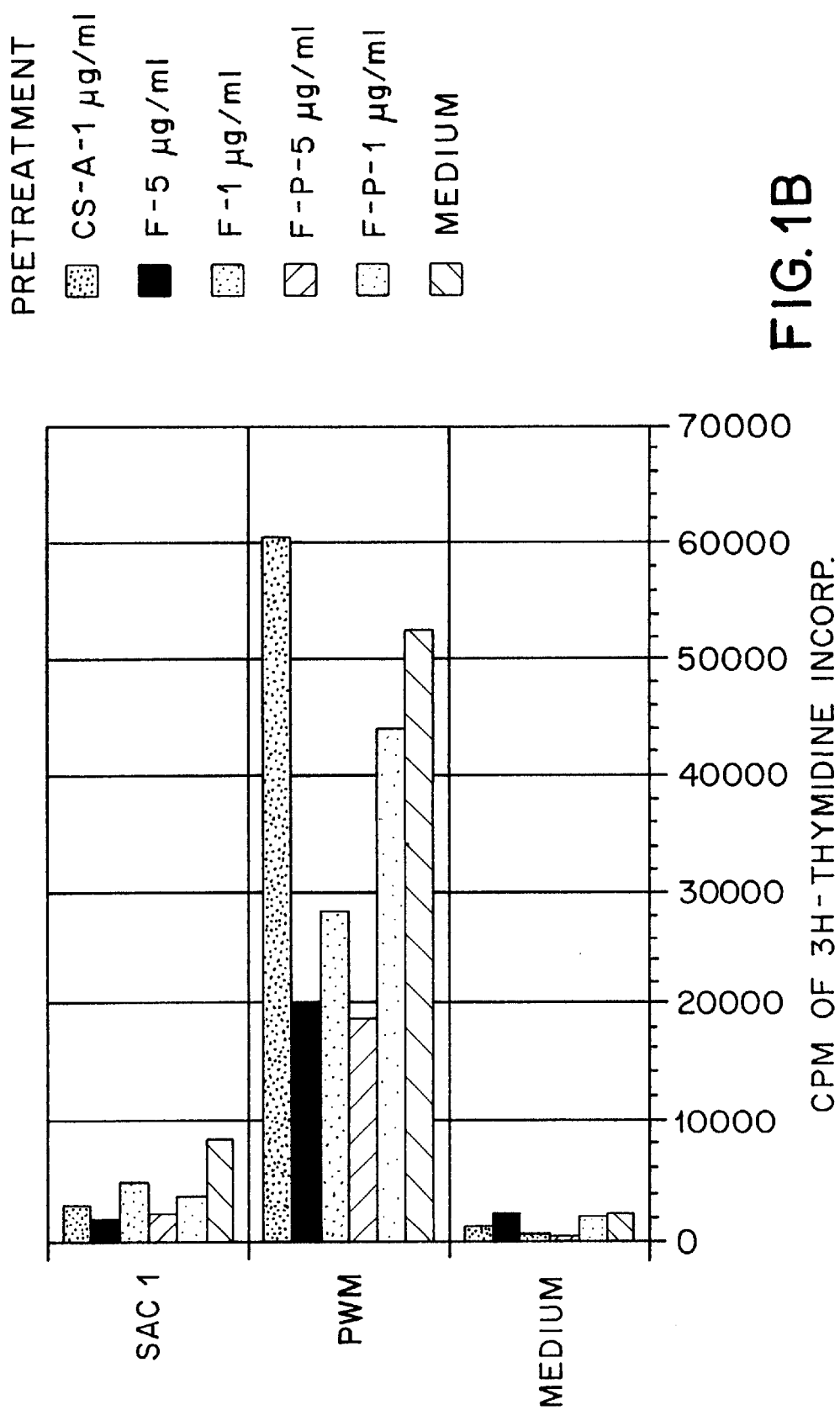

The results in FIG. 1 demonstrate that both the parent (F) and phosphorylated (F-P) drug can suppress the T (FIG. 1A) and B (FIG. 1B) lymphocyte's ability to respond to mitogen. It was of interest to see that B lymphocytes were more sensitive to the drugs effects as compared to the T lymphocytes. This is in contrast to the report by Boldt et al. (17), where T cells were shown to be more sensitive to the phosphorylated compound in vivo.

Additional experiments with PBMC enriched for T and B lymphocytes demonstrated that the B lymphocyte sensitivity to FLP was a general phenomenon (Table II).

TABLE II

Effect of Drug Pretreatment on T and B
Lymphocyte Responses to Mitogen Stimulation

| | BC5* | BC6 | BC7 | BC5 | BC6 | BC7 |
|---|---|---|---|---|---|---|
| | % Suppression | | | | | |
| | T LYMPHOCYTES | | | | | |
| | CON A (5 µg/ml) | | | PHA-P (5 µg/ml) | | |
| FLP-1** | 6 | 4 | 16 | 24 | 0 | 25 |
| FLP-5 | 29 | 29 | 40 | 32 | 15 | 50 |
| CSA-1 | 10 | 5 | 62 | 21 | 24 | 70 |
| | B LYMPHOCYTES | | | | | |
| | PWM (1 µg/ml) | | | SAC I (1/60,000) | | |
| FLP-1 | 59 | 11 | 16 | 14 | 0 | 55 |
| FLP-5 | 47 | 40 | 65 | 5 | 49 | 73 |
| CsA-1 | 34 | 0 | 0 | 0 | 0 | 63 |

*Leukocyte preparation number
**µg/ml of drug

Peripheral blood mononuclear cells enriched for either T or B lymphocytes were incubated for 18 hrs in complete S-10 medium at 37° C. in 12×75 mm culture tubes at $5 \times 10^5$ cells/ml. The cells were then washed in S-10 and cultured in triplicate for either 3 (T lymphocytes) or 6 (B lymphocytes) days at $2.5 \times 10^4$/well in round bottom 96-well microtiter plates in S-10 medium at 37° C. and a 5% $CO_2$ humidified atmosphere. The wells were pulsed with 1 µCi 3H-thymidine for the last 18 hr of culture, harvested onto glass fiber filters, and counted with 7 ml Cytoscint with a LKB Rackbeta scintillation counter. The results are reported as "percent Suppression":

% Suppression={1−(mean cpm exp./mean cpm stim control)}×100

TABLE III

RANGE OF CD20/CD5, CD20/CD5/SIgM, AND CD20/CD5/sIgG B
LYMPHOCYTES IN NORMAL INDIVIDUALS (n = 10)
% of Total Lymphocytes

| Cell Type | Mean | Range |
|---|---|---|
| CD5 | 71 | 62–78 |
| CD20 | 8 | 3–17 |
| CD20/CD5 | 6 | 4–9 |
| CD20/CD5/sIgG | 1.9 | 0.7–2.8 |
| CD20/CD5/sIgM | 1.6 | 0.4–2.7 |

Figure 2A:
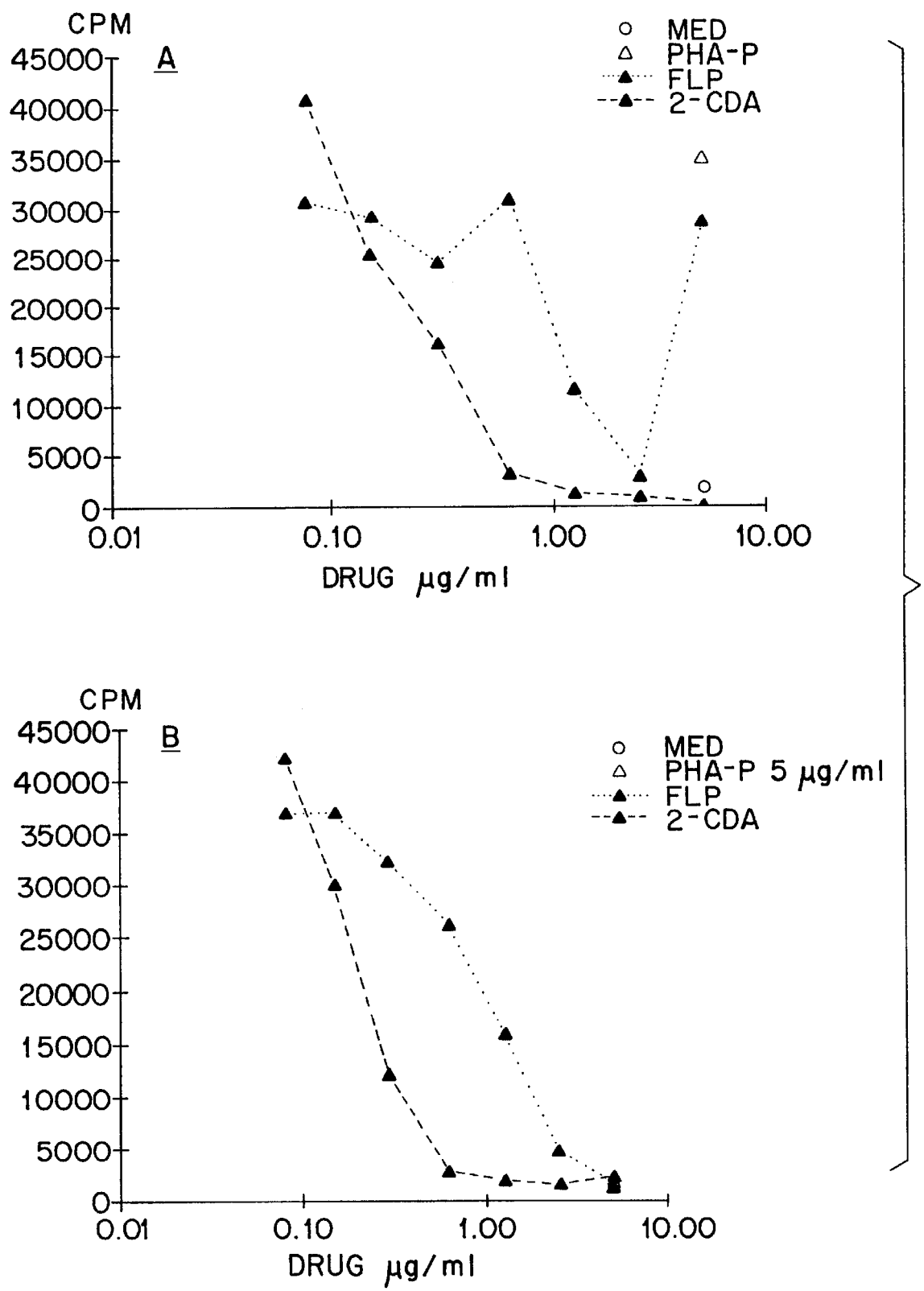
FIGS. 2a and 2b show a comparison of fludarabine-5'-monophosphate with 2-chlorodeoxyadenosine on T and B lymphocyte proliferative response to mitogens.
Figure 2B:
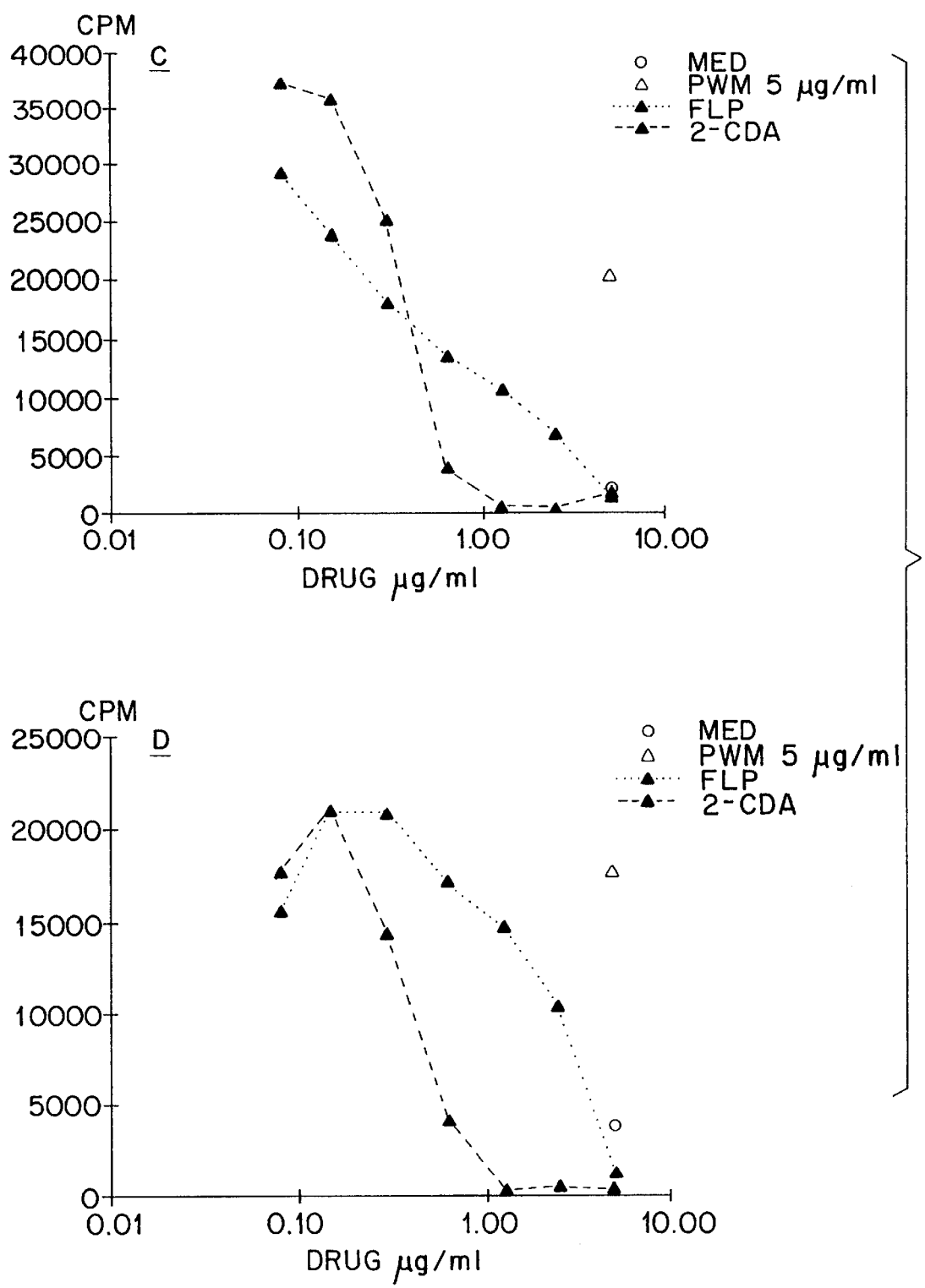

The adenosine analog 2-chlorodeoxyadenosine (2CDA) has also been reported to have significant cytotoxic and immunosuppressive effects on normal lymphocytes (10,13). In dose response studies with PBMC enriched for T or B lymphocytes stimulated with mitogen, FLP was seen to have similar effects to 2CDA (FIGS. 2A–B).

Example 2
Effect of FLP on B lymphocytes in culture

The effect of FLP on B lymphocytes was investigated further. A dose range of drug between 0.1–5.0 µg/ml was performed on PBMC enriched for B lymphocytes cultured for 48 hr with and without the mitogen PWM (FIG. 3). At the end of the culture period, the cells were washed, stained, and analyzed by flowcytometry for viable CD20 positive B lymphocytes.

The results illustrate two points. First, stimulation of the enriched B lymphocytes slightly increased the number of CD20 positive cells from 26% to 29%. Although the increase is small with no or low amounts of drug (0.1 µg/ml), this increase of CD20 staining cells over the medium control was constant throughout the effective dose range of the drug. Second, the effect of the drug was not evident until 0.5 µg/ml. This is approximately the same FLP concentration where suppression of mitogen-induced proliferation is first evident (FIG. 2).

The results shown above suggest that there is a significant effect on the B lymphocyte population. Studies were then performed to investigate the effect of the drug on mitogen-induced immunoglobulin production. Previous studies by other investigators have demonstrated that incubation of normal PBMC enriched for B lymphocytes with *Staphylococcus aureus* Cowan I (SAC) can induce preferential production of IgM and IgM-RF during a 10 day in vitro culture period (58).

Experiments were conducted that sampled supernatants and cells at 5 and 10 days culture with various amounts of drug. The effect of FLP seen at 5 days (FIG. 4) of culture were similar to that seen at 48 hrs (FIG. 3). The presence of SAC and rIL-2 in the culture increased the number of CD5 positive CD3 (7 to 22%) and CD20 (3 to 7.5%).

This CD5 result correlates with other reports describing the CD5 marker as an activation or differentiation antigen (59).

The presence of 0.1 µg/ml of FLP had minimal effect on the relative percent of CD20, CD20/CD5, and CD3/CD5 staining cells, but a dose-dependent decrease in these subpopulations of cells was seen from 0.5 µg to 5.0 µg/ml. No apparent specificity for a particular cell subset was apparent. These results are reported as "percent total lymphocytes" as described in the Materials and Methods section (see above).

When supernatants from similar 5 day cultures were examined for the production of IgM by EIA, 1.0 µg/ml of FLP was sufficient to bring detectable IgM to background levels (FIG. 5). Similar results were seen when supernatants from 10 day cultures were examined (FIG. 6). The addition of recombinant human IL-6 (rIL-6) to the cultures modulated the effect of FLP on IgM accumulation in 5 day cultures (FIG. 5). This effect was not seen in 10 day culture supernatants supplemented with exogenous rIL-6. There was some indication of breakthrough in IgM production in the 10 day cultures. This may be due to the breakdown of the drug or the presence of resistant B cells in the prolonged culture period.

Cytofluorometric analysis of the B lymphocytes at the end of the 5 day culture period indicated that the drug had a significant effect on the CD20/CD5 positive B lymphocyte subpopulation (Table IV). The presence of rIL-6 did not affect this phenomenon.

TABLE IV

Effect of FLP treatment on phenotype of 5 day
in vitro cultured normal lymphocytes
% Viable (% Total)

| | | Med | | SAC/rIL-2 IL-6 | | +FLP | |
|---|---|---|---|---|---|---|---|
| Input | | − | + | − | + | − | + |
| CD20 | 59 | 58 | 69 | 53 | 59 | 64 | 60 |
| CD20/5 | 14 | 4.7 | 7.7 | 8 | 9 | 1.8 | 1.9 |

*1.0 µg/ml FLP + SAC/rIL-2 (50 µ/ml)

Example 3
Effect of FLP on immunoglobulin accumulation

The next series of experiments examined the effect of FLP on IgM, IgG, and IgM-RF accumulation over both 5 and 10 day culture periods. Previous reports have demonstrated that maximum accumulation of immunoglobulin, particularly IgM, in cultures stimulated with SAC and rIL-2, is reached in 10 days (58). The results shown in FIG. 6 indicate that measurable IgM is present in culture supernatants after 5 days. Therefore, peripheral blood mononuclear cells enriched for B lymphocytes by one nSRBC rosetting step were continuously cultured with various concentrations of FLP and SAC plus rIL-2.

Figure 7B:
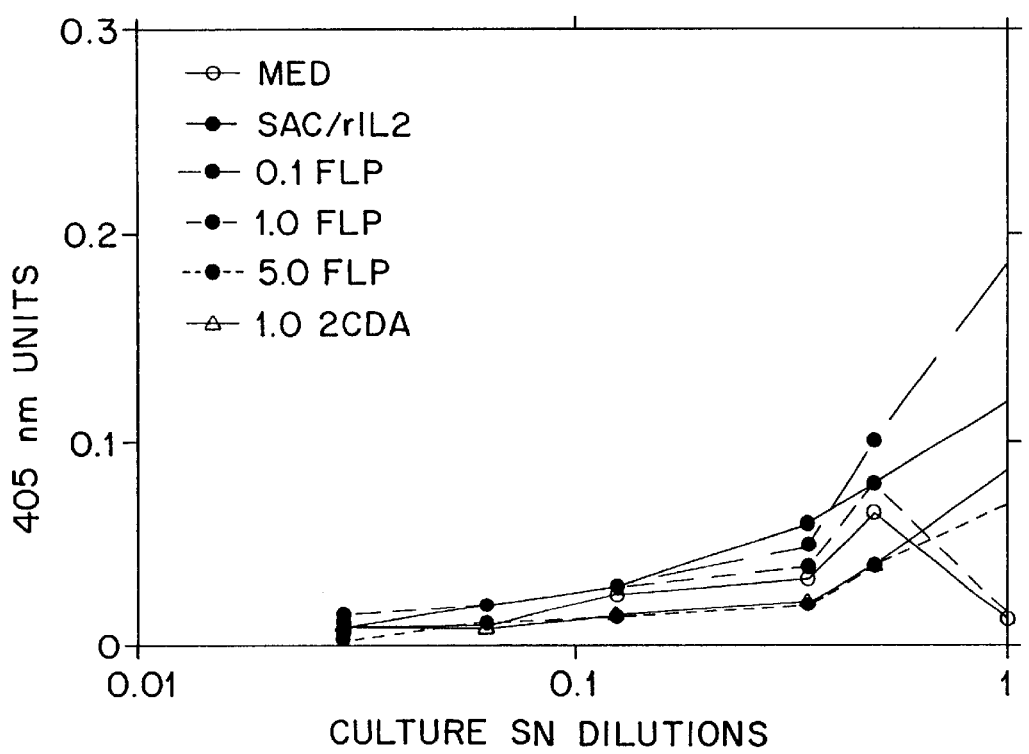

Supernatants analyzed for IgM and IgG (FIGS. 7A and B) exhibited measurable amount of both isotypes at 5 days. The amount of immunoglobulin was in the nanogram range, as determined by a standard curve (data not shown). One hundred nanograns per ml of FLP had minimal effect on both IgM and IgG production, although this amount of drug seemed to enhance the IgG production (FIG. 7B). One microgram per ml of FLP had an intermediate effect on IgM production, and 5 $\mu$g/ml was sufficient to block any measurable IgM accumulation. The IgG results were more mixed, and may be a result of the short culture period. One microgram per ml of 2CDA was sufficient to block both IgM and IgG production.

Figure 7C:
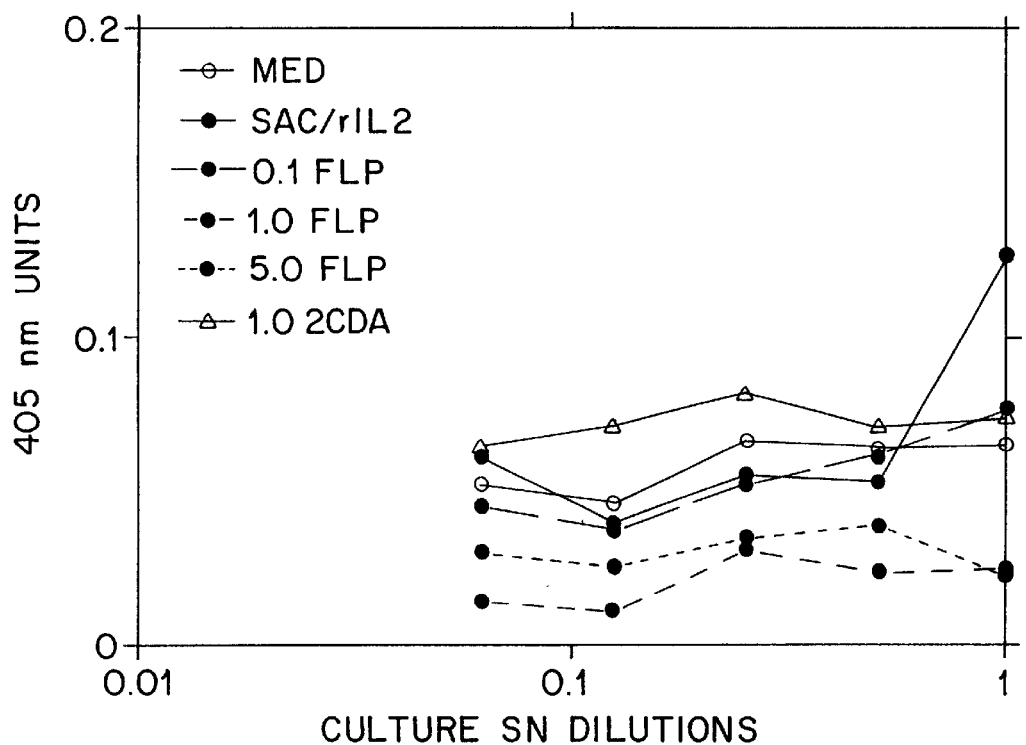

At five days, the amount of IgM-RF production induced by SAC plus rIL-2 was small but measurable (FIG. 7C). It is interesting to note that while FLP at both 1 and 5 $\mu$g/ml reduce the measurable IgM-RF, the drug 2CDA at 1 $\mu$g/ml has less effect. This is in contrast to that seen with the total IgM.

Figure 8C:
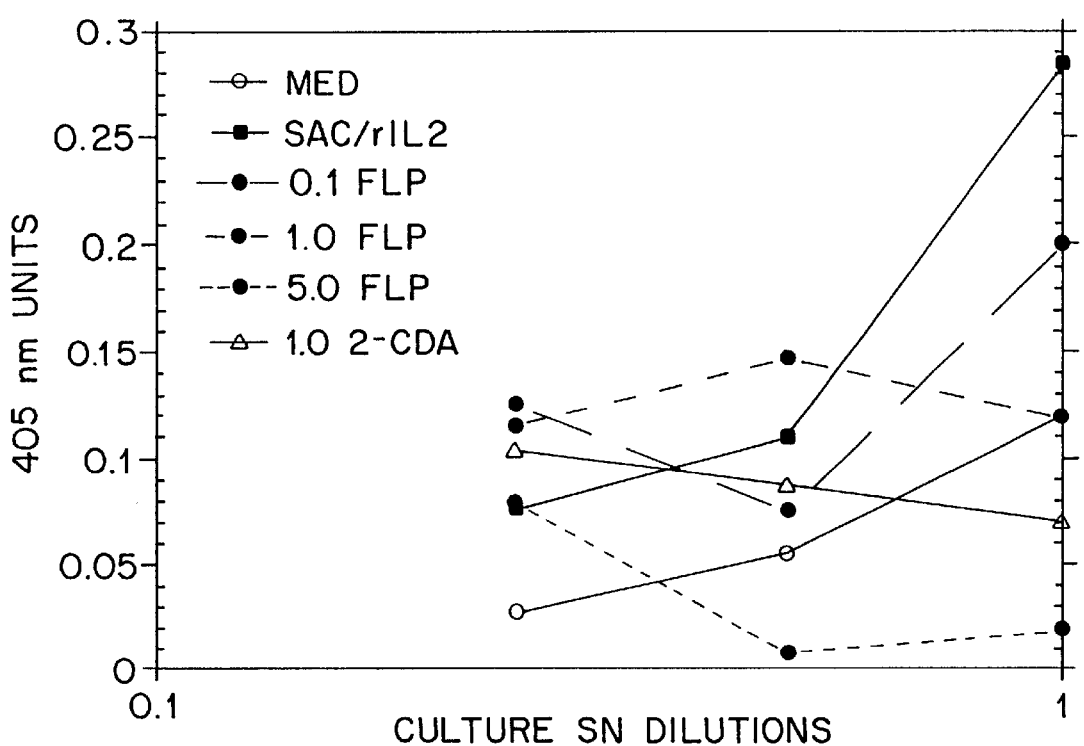

The amounts of both IgM and IgG at 10 days were increased approximately seven times that seen at 5 days of culture. Both isotypes were in the microgram range as determined by regression analysis (data not shown). FLP again had minimal effect at 0.1 $\mu$g/ml, but both 1 and 5 $\mu$g of FLP reduced the accumulation of both isotypes 80% and 98%, respectively. (FIGS. 8A and B). One microgram per ml of 2CDA was also able to block the accumulation of both isotypes. The accumulation of IgM-RF was also increased at 10 days with SAC plus rIL-2 (FIG. 8C). The effect of 0.1 $\mu$g/ml of FP was more pronounced on IgM-RF production (50% of control). It was again interesting to see that 5 $\mu$g of FLP were able to decrease the level of measurable IgM-RF below the medium control levels. This parallels what was seen at 5 days (FIG. 7C). These results suggest that when a significant amount of T cells are present in the culture, a measurable amount of spontaneous IgM-RF is seen, and that FLP is able to affect this accumulation. The drug 2CDA demonstrates characteristics similar to FLP at 1 $\mu$g/ml.

The effect of T cells in the culture environment has been shown to also support IgM-RF production when stimulated with anti-CD3 (59). The presence of exogenous rIL-2 may play a role in the T cells ability to help B cell produce RF. Supernatants examined at 5 days of culture showed that FLP at 0.1 and 0.5 $\mu$g/ml were able to reduce the amount of both IgM and IgM-RF accumulation in cultures containing either rIL-2 or 20% conditioned medium from PHA-P T cells (FIGS. 9A and C). This was not seen in the IgG accumulation in cultures supplemented with T cell conditioned medium (FIG. 9B). These results suggest that exogenous lymphokines other than IL-2 and IL-6 may influence the drug's effect on IgG production. The effect of FLP on IgM-RF production was less pronounced at 5 days in cultures containing the T cell conditioned medium. This set of experiments also suggests that any contributions to IgG production by the endogenous contaminating T cell population in the wells was overcome by the addition of FLP to the culture system.

Example 4

Primary effect of FLP on lymphocytes

The next investigation examines what part of the life cycle the primary effect of FLP influences.

1. Washout test on 6 day B lymphocyte cultures

The B lymphocytes are cultured with SAC +rIL-2 under the following conditions:
   1. 0 to 72 hr + drug (0.1–0.5 8g/ml), wash, continue culture for additional 72 hr
   2. 0 to 72 hr, wash, add drug for additional 72 hr culture
   3. No drug for 6 days (wash at 3 days)
   4. Drug in continuous culture for 6 days At the end of the culture period, the supernatants are assayed for IgM, IgG, and IgM-RF.

The results confirm that FLP has its primary effect on early stage B lymphocyte proliferation/differentiation. (Results not shown.)

2. Sensitivity of B cell subtypes to FLP

B lymphocytes are incubated with drug (0.1–1.0 $\mu$g/ml) for 48 hr, followed by 5 to 10 days culture with SAC/rIL-2. The supernatant is then assayed at 5 and 10 days for IgM, IgG, and IgM-RF. Analyze the cells by flowcytometry at day 5 for CD20, CD20/CD5, CD5/sIgM, CD5/IgG, CD20/5/sIgM, and CD20/5 sIgG.

CD5 positive B cells are found to be more sensitive to drug and the frequency of sIgM and sIgG cells are decreased, reflecting the blockage of immunoglobulin production. (Data not shown.)

Example 5

Rat model of Rheumatoid Arthritis and FLP

Intradermal immunization of DBA/1 (H-$2^q$) male mice with homologous type II collagen (CII) induces symptoms characteristic of arthritis between 6–18 weeks after immunization. This chronic, progressive polyarthritis involving the four paws is characterized by joint swelling and erythema localized in the single metatarsophalangeal and interphalangeal joint. The evolution of the disease fluctuates between remissions and exacerbations. Varying levels of autoantibodies to mouse CII are seen, but have little or no relation to disease activity.

A number of drugs have been tested in the two types of Type II collagen induced arthritis. The anti-lymphocytic drug cyclosporin A (CsA) was able to prevent development of the disease if administered prior or at the same time as the immunization with Type II collagen in Sprague-Dawley rats (44). An enhancement of the disease was seen if the drug was given after collagen administration but before the clinical phase of the disease. The antibody responses were either suppressed or unaffected.

The DBA/1J mouse model of Type II collagen-induced arthritis was used to evaluate a number of current and proposed therapies for RA (45). The results were mixed, which is illustrated by the fact that D-penicillamine actually led to an early onset of the disease.

Human type II collagen-induced arthritis in rats is an autoimmune model of RA (46). The diabetes-resistant (DR) subline of the diabetic BB strain of rat has been shown to have a similar genetic background to that found in the human disease with respect the third hypervariable region of the HLA DR beta gene. This sequence of five amino acids has been termed the "susceptibility sequence" or "SS." When injected with human Type II collagen, arthritis develops rapidly by day 10 with a very high incidence. The pathology of the disease is remarkably like that seen in the human disease with respect to rapid, bilateral cartilage resorption, and the predominant humoral response to the cyanogen bromide (CN) 11 fragment of human cartilage. This model may be a more valid indicator of drug efficacy.

The study involves two treatment schedules (47). In Schedule I, FLP is injected on a daily basis on days 0–10 at doses of 1 and 10 mg/kg/day. In Schedule II, FLP is injected at days 10–20 at 1 and 10 mg/kg/day. This study demonstrates that FLP was active following onset of disease. Clinical, histological, EIA, and flowcytometry are employed to follow the progress of the disease. Correlation with the in vitro data using human PBMC is seen.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

1. S. L. Dahl, 1989, "Rheumatic Disorders," Chap. 72:1175.
2. Mackay and Rawley, 1988, Postgrad. Med. J. 64:522.
3. R. L. Wilder, 1990, "Rheumatoid Arthritis and Related Conditions," Current Opinion in Immunology, 2:613.
4. Scott-Levin Associates, Physician, Drug and Diagnosis Audit (January–December 1991).
5. Anti-Arthritic Agents, Health Industries Handbook, SRI International, Menlo Park, Calif., November 1991.
6. Shiroky, Yocum, Wilder, Klippel, 1989, *Concepts of Immunopath*, eds., Cruse and Lewis, 7:106.
7. J. M. Kremer, 1990, Geriatrics, 45(12):43.
8. C. A. Bowles, 1989, Arthritis Rheum. 32:523. (Abstract)
9. G. Kingsley, G. Panayi, and J. Lanchbury, 1991, Immunology Today, 12(6):177.
10. D. A. Carson, D. B. Wasson and E. Beutler, 1984, PNAS(USA) 81:2232.
11. T. J. M. Ruers, W. A. Burman and C. J. van der Linden, 1987, J. Immunol., 138(l):116.
12. L. D. Piro, C. J. Carrera, E. Beutler and D. A. Carson, 1988, Blood 72(3):1069.
13. D. A. Carson, J. Kage, J. E. Seegmiller, 1978, J. Immuno. 121:1726.
14. D. A. Carson, D. B. Wasson, R. Taetle, and A. Yu, 1983, Blood 62(4):737.
15. C. J. Carrera, C. Terai, M. Lotz, J. G. Curd, L. D. Piro, E. Beutler and D. A. Carson, 1990, J. Clin. Invest. 86:1480.
16. C. K. Edwards, L. M. Watts, M. D. Hatfield and D. R. Burcherding, 1990, J. Clin. Biochem. Supp. 15E. "Mol. Biol. and Immunopath. of RA," Lake Tahoe, Calif., Abstract #O 103.
17. Boldt, von Hoff, Kuhn and Hersh, 1984, Can. Res. 44:4661.
18. Advances in Leukemia and Lymphoma. 1(l):10.
19. Hersh et al., 1986, Cancer Chemother. Pharm. 17:277.
20. V. I. Arranis, 1989, Can. Invest. 7(2):129.
21. Cheson et al., 1988, Amer J. Hemat. 39:152.
22. A. S. Freedman, 1990, Hematol. Oncol. Clin. of N. Amer. 4(2):405.
23. Foon et al., 1990, Ann. Intern. Med. 113:525.
24. P. Youinou, L. MacKenzie, P. Katsikis, G. Merdrignac, D. A. Isenberg, N. Tuallon, A. Lamour, P. le Goff, J. Jouquan, A. Drogou, S. Muller, B. Genetet, H. M. Moutsopoules and P. M. Lydyard, 1990, Arthr. and Rheum. 33(3):339.
25. K. Hayakawki, 1990, Curr. Opin. Immunol. 2:582.
26. P. Casali, and A. L. Notkins 1989, Immun. Today 10(11):364.
27. H. E. Jasin, 1991, Cell. Immunol. 136:133.
28. S. E. Burasteros, P. Casali, R. L. Wilder, A. L. Notkins, 1988, J. Exp. Med. 168:1979.
29. Kazbay, K. Osterland, 1990, Clin. Exp. Rheum. 8(3):231.
30. Smith and Olsen, 1990, J. Rheum. 17(6):833.
31. H. Becker, C. Weber, S. Storch, K. Federlin, 1990, Clin. Immunol. Immunopath. 56(2):219.
32. S. Ackerman, 1990, "Anti-CD5 in RA," Presented at Early Decisions in DMARD Development II, September 13–14, San Francisco, Calif.
33. H. van de Verde, I. van Hoegen, W. Luo, J. R. Parnes and K. Thieleman, 1991, Nature 351(6328):662.
34. Fludara-I.V.™ NDA Submission, V2.5 of 2.45; Animal Subchronic Studies 5.4.3. TBT03-002 (#592-009, Dog, 110888); TBT03-003 (#B10-52004, Rat,111588).
35. Ibid. 2.8.5 Summary of Safety; 2.8.5.1.2.2 Hematological events.
36. Ibid. 2.9.1.3 Risks.
37. Boldt et al., 1984, Can. Research. 44:4661.
38. G. E. Umbach, V. Hug et al., 1984, Invest. New Drugs, 2:263.
39. G. E. Umbach, V. Hug et al., 1985, J. Can. Res. Clin. Oncol. 109:130.
40. J. L. Ascensao, J -W. Chiao, R. Lincoln, and T. Ahmed, 1991, Submitted for publication.
41. ARA criteria in Cecil's Textbook of Medicine, p. 1911–7, Wyngaarden and Smith, eds., Saunders, Philadelphia, 1985.
42. Pilot Study submitted by Dr. Antonio Pezzotto, 1991, Med. Klinik und Poliklinik V, Univ. of Heidelberg, Hospital str. 3, D-6900, Heidelberg.
43. R. I. Fox, C. A. Robinson, G. W. Williams, J. G. Cord, C. W. Colwell, and T. F. Bumol., Chap 8. in Immunomodulators in the Rheumatic Diseases, Marcel Dekkar, Inc., New York and Basal, 1990.
44. Kaibara, Hotokebuchi, Takagishi and Katsuki, 1983, J. Exp. Med. 158:2007.
45. Phadke, Fouts, Parrish and Butler, 1985, Immunopharmacology 10:51.
46. W. C. Watson, Thompson, Terato, Cremer and Kang, 1990, J. Exp. Med. 172:1331.
47. W. C. Watson, personal communication.
48. M. J. Keating, 1990, Seminar in Oncology, 17(5):49, Suppl. 8 (Oct.).
49. P. J. Kelly et al., 1992, J. Immunol., 148(5):1294.
50. J. F. Bach, 1989, Trans. Proceed. 21(3) Suppl. 1 (June):97–113.
51. H. O. McDevitt, Proceedings: Early Decisions in DMARD Develop. II., Sept. 13–14, 1990, San Francisco, Calif., Arthritis Foundation, Atlanta, Ga., pp. 3–7.
52. A. A. Sinha et al., 1990, Science 148:1380.
53. R. R. P. de Vries et al., 1988, "HCA and Autoimmunity in Perspectives on Autoimmunity," CRC Press, Boca Raton, Fla., pp. 1–18.
54. Ibid., "Chap. 5", pp 111–134.
55. Y. Shiokawa, 1988, "Lobenzarit (CCA), the Pharmacology of Lymphocytes: Handbook of Experimental Pharmacology", Vol. 85 (ed. by M. A. Bray, J. Marley, Berlin, Springer-Verlag).
56. Y. Shiokawa et al., 1989, "A multicenter double-blind controlled study of lobenzarit, a novel immunomodulator, in rheumatoid arthritis," J. Rheum. 11:615.

57. Hirohata et al., 1992, "Regulation of B Cell Formation by Lobenzarit, a Novel Disease Modifying Drug," Arth. Rheum. 35(2):168.
58. Levinson et al., 1986, J. Clin. Invest. 78:612.
59. Vernino et al., 1992, Cell. Immunol. 139:185.

What is claimed is:

1. A method of treating an autoimmune disease, comprising administering to a patient in need of such treatment an effective amount of fludarabine-5'-monophosphate.

2. A method of claim 1, wherein the disease is rheumatoid arthritis.

3. A method of claim 1, wherein the amount of fludarabine-5'-monophosphate is 1 to 10 mg/kg/day.

4. A method of preventing the occurrence of symptoms of an autoimmune disease, comprising administering to a patient in need of such treatment an effective amount of fludarabine-5'-monophosphate.

5. A method of claim 4, wherein the disease is rheumatoid arthritis.

6. A method of claim 4, wherein the amount of fludarabine-5'-monophosphate is 1 to 10 mg/kg/day.

7. A method of reducing the symptoms of an autoimmune disease, comprising administering to a patient in need of such treatment an effective amount of fludarabine-5'-monophosphate.

8. A method of claim 7, wherein the disease is rheumatoid arthritis.

9. A method of claim 7, wherein the amount of fludarabine-5'-monophosphate is 1 to 10 mg/kg/day.

10. A method of claim 1, wherein the disease is psoriasis.

11. A method of claim 4, wherein the disease is psoriasis.

12. A method of claim 7, wherein the disease is psoriasis.

13. A method of claim 1, whereby adverse autoimmunological effects of T or B cell production are reduced or prevented.

14. A method of claim 4, whereby adverse autoimmunological effects of T or B cell production are reduced or prevented.

15. A method of claim 7, whereby adverse autoimmunological effects of T or B cell production are reduced or prevented.

* * * * *

UNITED STATES PATENT AND TRADEMARK OFFICE
CERTIFICATE OF CORRECTION

PATENT NO.    : 6,337,333 B1
DATED         : January 8, 2002
INVENTOR(S)   : Martin A. Giedlin It is certified that error appears in the above-identified patent and that said Letters Patent is hereby corrected as shown below:

Title page,
Item [*] Notice, delete the first paragraph

Signed and Sealed this

Fourth Day of May, 2004

JON W. DUDAS
*Acting Director of the United States Patent and Trademark Office*